United States Patent [19]
Ferreira

[11] Patent Number: 4,805,459
[45] Date of Patent: Feb. 21, 1989

[54] ULTRASONIC TESTING METHOD

[75] Inventor: Nicholas C. Ferreira, Manchester, Conn.

[73] Assignee: Aerospace Testing Lab, Inc., Windsor, Conn.

[21] Appl. No.: 162,051

[22] Filed: Feb. 29, 1988

[51] Int. Cl.⁴ .................................... G01N 29/00
[52] U.S. Cl. ............................... 73/620; 73/627
[58] Field of Search ............. 73/618, 619, 620, 628, 73/629, 615, 622, 633, 627

[56] References Cited

U.S. PATENT DOCUMENTS

| | | | |
|---|---|---|---|
| 3,395,572 | 8/1968 | Sinclair | 73/629 |
| 3,939,697 | 2/1976 | Lund et al. | 73/620 |
| 4,457,174 | 7/1984 | Bar-Cohen et al. | 73/620 |
| 4,557,145 | 12/1985 | Perdijon | 73/633 |

Primary Examiner—Stewart J. Levy
Assistant Examiner—Louis M. Arana
Attorney, Agent, or Firm—Victor E. Libert

[57] ABSTRACT

An ultrasonic sound echography technique is disclosed in which echo-masked zones of the workpiece are reduced by utilizing particular orientations of the beam of ultrasonic sound relative to formations in the workpiece. Echo-masked zones result from formations in the workpiece which reflect the ultrasonic sound waves back to the probe and therefore mask the much smaller echoes from anomalies, if any, in the workpiece. Instead of the conventional orientation of the beam, in which the scanning plane in which the beam lies is oriented perpendicularly to formations, the scanning planes are selected so as to be non-perpendicular with respect to such formations and to minimize the amount of masking echoes from the formations.

15 Claims, 9 Drawing Sheets

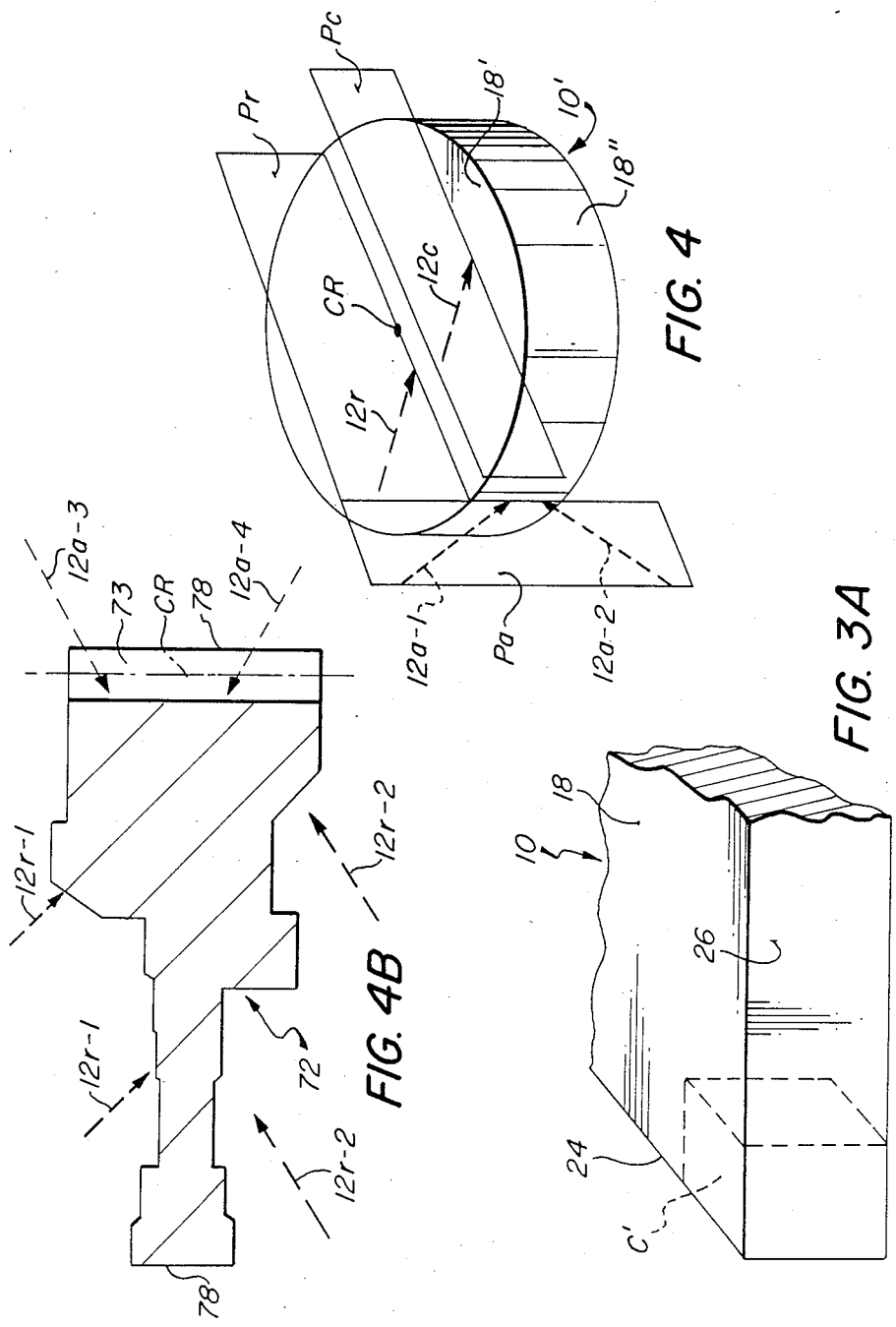

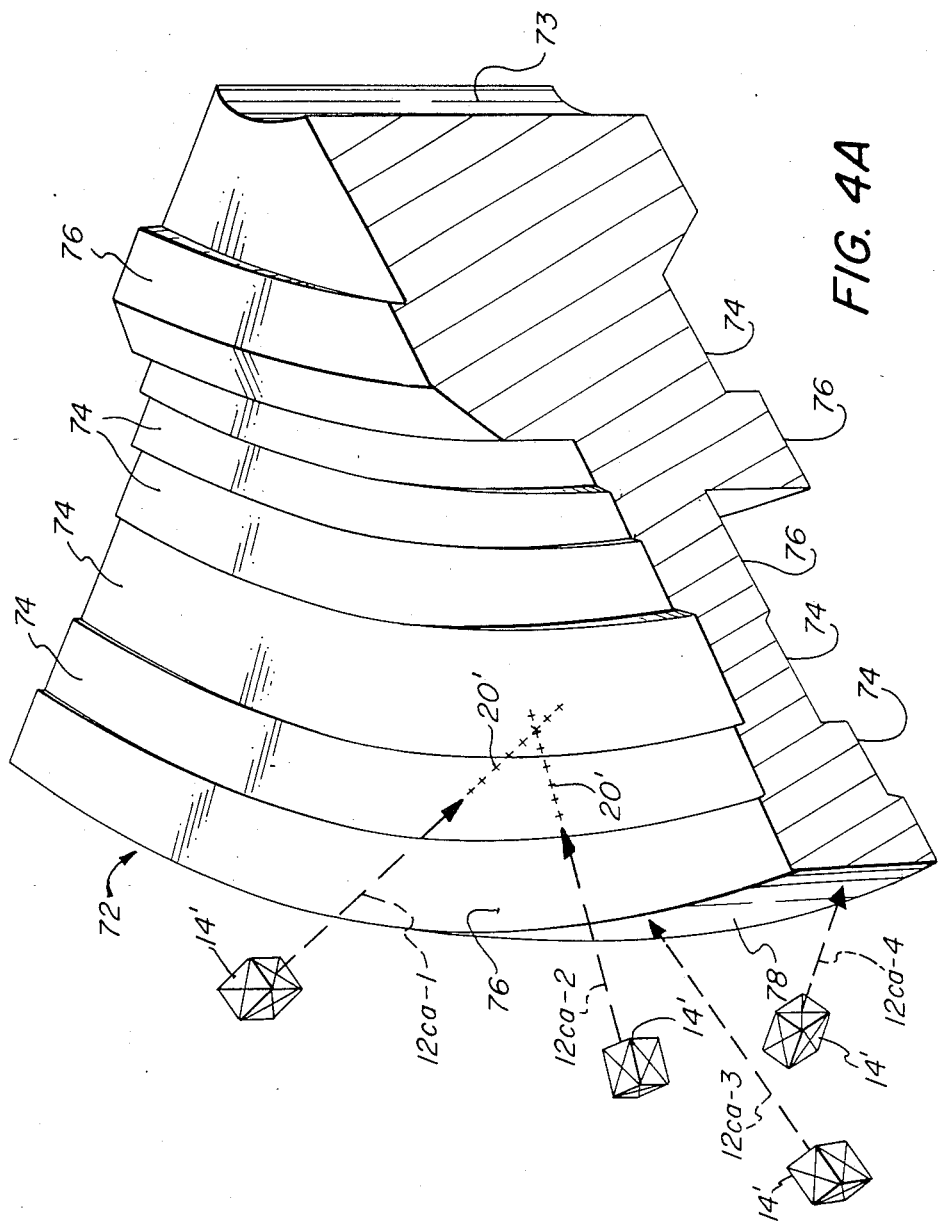

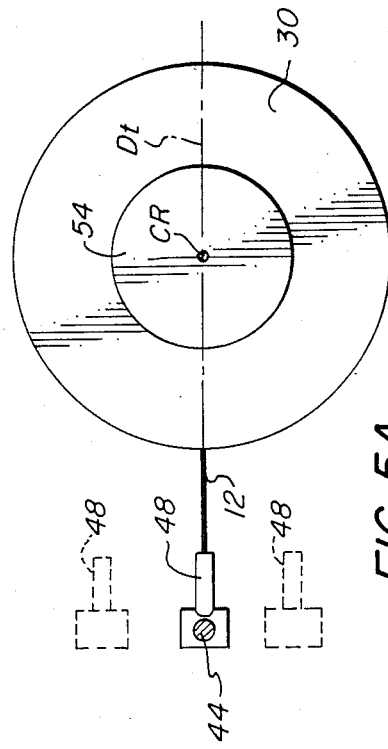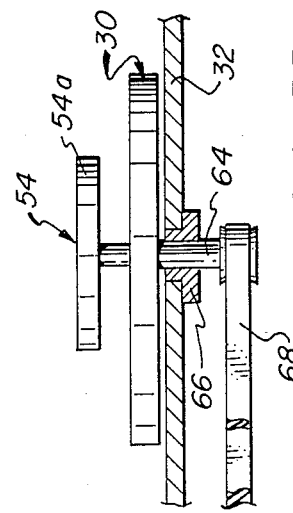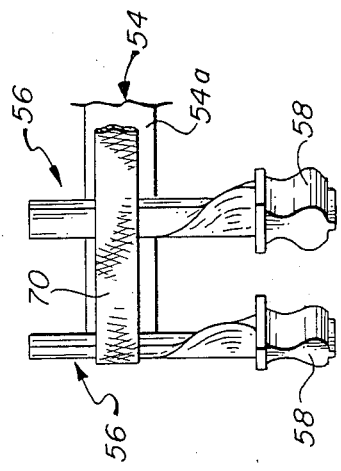

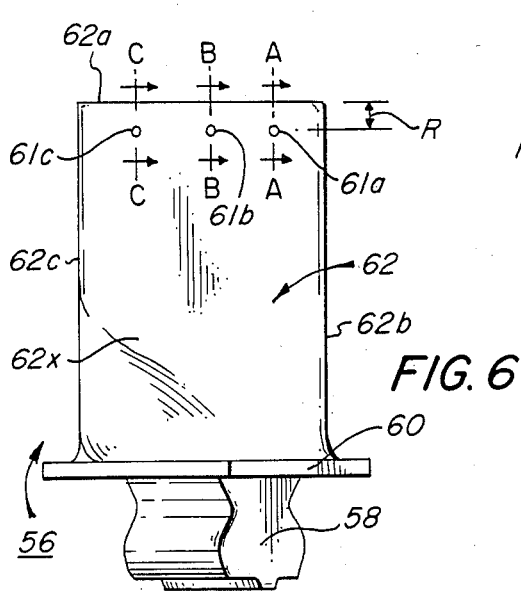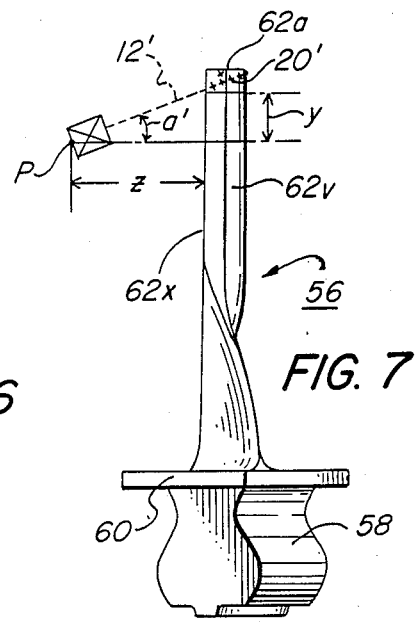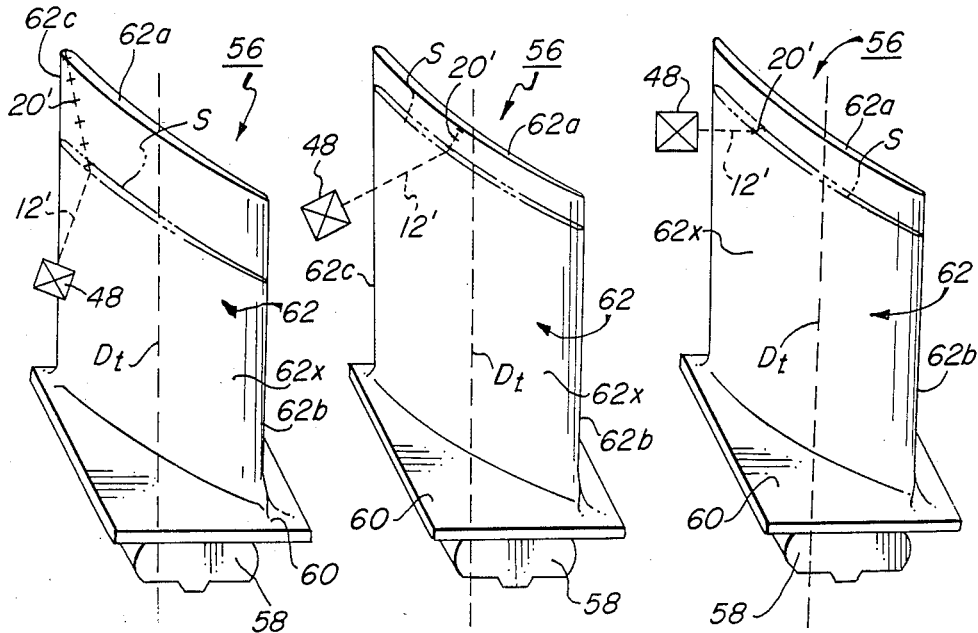

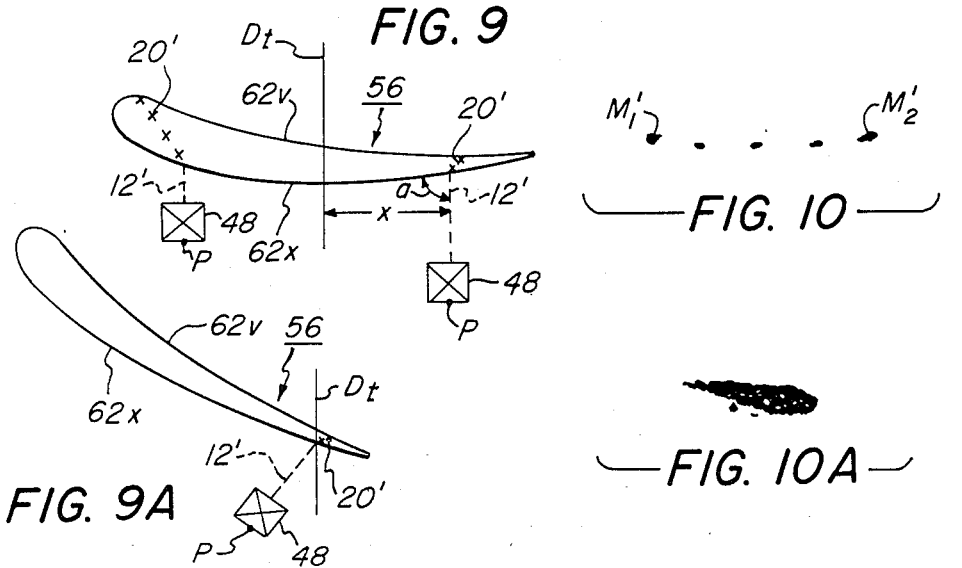
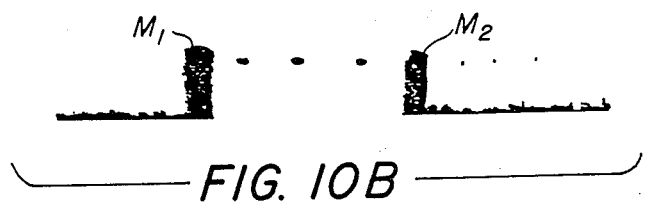
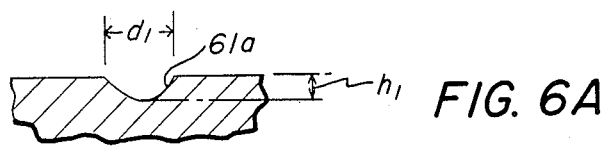
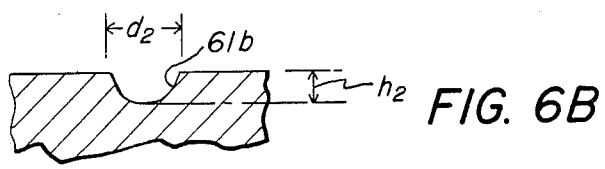
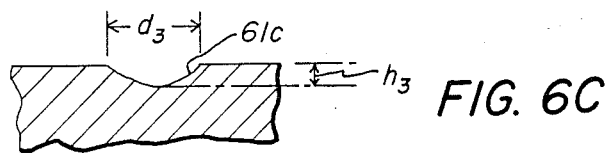

ULTRASONIC TESTING METHOD

BACKGROUND OF THE INVENTION

1. Field of the Invention

The present invention is concerned with ultrasonic testing generally, and more particularly with echo-type ultrasonic testing, sometimes referred to as ultrasonic scanning echography, in which a transducer is utilized to generate a beam of ultrasonic sound which is reflected back to the transducer from a workpiece being inspected. The reflected ultrasonic sound waves are displayed to detect anomalies in the workpiece. Such techniques are extensively used for non-destructive testing of welded or solid pieces in which structural anomalies such as cracks, pinholes, discontinuities and the like cause characterisic sound wave echoes which indicate the existence and position of such anomalies.

2. Description of Related Art

Perdijon U.S. Pat. No. 4,557,145 discloses an apparatus for ultrasonic testing of workpieces in which the transducer is rotated to define a conical surface about an axis which is orthogonal to the inspection surface of the workpiece, as illustrated in FIG. 1 of the patent. The rotating transducer is translated across the surface of the workpiece and the patentee states that the ultrasonic sound pulses are timed so that each zone to be scanned receives at least two pulses corresponding to different azimuth angles about a common axis of rotation.

Garner et al U.S. Pat. No. 4,685,966 shows an apparatus which enables compound movement of the ultrasonic probe in order to maintain the angle of incidence at or close to perpendicular to the surface of the workpiece, even when the latter is a compound curved surface. The patent discloses rotation about both a horizontal and vertical axis (e.g., column 2, line 45 through column 3, line 19) with the objective of always maintaining the angle of incidence substantially perpendicular to the test surface.

Spencer et al U.S. Pat. No. 3,765,229 discloses an ultrasonic scanner which is interchangeable between an oscillating mode to examine curved panels as illustrated in FIG. 4, and a translational mode for the examination of flat panels. See the paragraph headed "Operation" in column 4 of the patent.

Singh et al U.S. Pat. No. 4,502,331 shows ultrasonic inspection of turbine disc rims in which, as illustrated in FIG. 6, the transducer is skewed in different passes at 45 and 60 degrees in order to inspect, respectively, the concave and convex sides of the "steeples" of the workpiece.

Conventional ultrasonic echo pulse testing, sometimes referred to as "echography", generally examines a workpiece by scanning a surface or region of the workpiece, often by carrying out two mutually perpendicular series of passes along the same surface or region. Thus, a rectangular region may be scanned from top to bottom in a first series of parallel, north-to-south passes and from side to side in a second series of parallel east-to-west passes. In the case of a disc-shaped workpiece, the scanning may be conducted along one or both of its circular-shaped surfaces and along its cylindrical-shaped surface. Conventional respective orientations of the test probe relative to the workpiece in respective series of passes are sometimes referred to as axial, radial and circumferential orientations, as described in more detail below. The orientations employed may be mandated by the direction of metal grain flow in forged articles, and by the desire to simplify the test set-up. This conventional approach accepts the uninspectability of certain regions of a workpiece because of reflection of the ultrasonic sound pulses from lands, bosses, ridges, grooves, rims or other return-reflecting formations or configurations of the workpiece. Such reflections, i.e., echoes, mask the much smaller echoes caused by anomalies in the workpiece. Even in the case of a simple shape, such as a flat, rectangular plate, the edges of the workpiece which are transverse to the direction of a given scan or series of scans are uninspectable because of ultrasound reflection to the probe from the edges. As a consequence, regions of the workpiece are either left uninspected, resulting in inherent risks and lower reliability of the tested part, or must be tested by other techniques such as X-ray, metal filings dispersion, and the like. The requirement for additional tests, usually carried out with different equipment, naturally increases substantially the test cost per workpiece. Even if the additional testing to inspect areas ininspectable by conventional orientation of the test probe is carried out with ultrasonic echo pulse testing on the same equipment, it requires a third and possibly additional series of inspection passes, as well as the calculation of probe positioning for additional set-ups, in order to scan as much as possible of the workpiece volume which is uninspectable with the conventional axial and circumferential probe orientation.

SUMMARY OF THE INVENTION

In accordance with the present invention there is provided an improvement in an ultrasonic sound scanning method for detection of ultrasonic sound-reflecting anomalies in a workpiece having an inspection surface and at least one return-reflecting formation which results in an echo-masked zone in the workpiece. The inspection surface may be flat or curved, e.g., convex. The method includes carrying out an inspection pass by (a) directing a beam of ultrasonic sound pulses from a probe along a beam axis through a transmission medium, e.g., water, and impinging the beam upon the inspection surface at a selected impingement angle and thence into the workpiece, (b) receiving echo pulses thereby reflected from the workpiece, (c) displaying the echo pulses to reveal those, if any, which indicate the existence of anomalies within the workpiece, and (d) traversing the beam in a pre-selected path along the inspection surface. The improvement provided by the present invention comprises making one or more first inspection passes with the probe oriented so that, relative to the workpiece, the beam lies within one or more first scanning planes which are non-perpendicular to at least one return-reflecting formation at its point or respective points of intersection with the first plane or planes, whereby to reduce the volume of the echo-masked some relative to that which would be generated with the probe oriented in a corresponding number of one or more scanning planes which are perpendicular to the at least one return-reflecting formation.

In accordance with another aspect of the present invention, the improved method includes making a second series of inspection passes with the probe oriented so that the beam of ultrasonic sound pulses (which may, but need not, be a focused beam) lies in a series of second scanning planes which intersect the first scanning planes. For example, the second scanning planes may be substantially perpendicular to the first scanning planes.

In one embodiment of the invention, a first series of the first inspection passes is made, so that the beam successively lies within a series of the first scanning planes.

In accordance with another aspect of the invention, there is provided a method of ultrasonic sound scanning for detection of ultrasonic sound-reflecting anomalies in one or more workpieces having inspection surfaces and one or more return-reflecting formations which result in one or more echo-masked zones in the workpiece. In this aspect, the method comprises establishing relative movement within a transmission medium between the one or more workpieces and a probe from which a beam of ultrasonic sound pulses emanates, and directing the beam along a beam axis through the transmission medium, and impinging the beam upon the inspection surface at a selected impingement angle and thence into the workpiece. The relative movement is maintained in order to traverse the beam in a pre-selected path along the inspection surface with the probe oriented so that, at least when the beam impinges the workpiece in the vicinity of the return-reflecting formations, the beam successively lies within a series of first scanning planes which are non-perpendicular to at least one of the return-reflecting formations at its respective points of intersection with the first scanning planes, whereby to reduce the volume of the echo-masked zone relative to that which would be generated with the probe oriented in a series of scanning planes which are perpendicular to the return-reflecting formation. As with other aspects of the invention, echo pulses reflected from the workpiece are received and displayed to reveal those pulses, if any, which indicate the existence of anomalies within the workpiece.

Other aspects of the invention will be apparent from the following description, including the drawings.

As used herein and in the claims, the following terms, whether used in the singular or plural forms, have the stated meanings:

The term "return-reflecting formation" means a formation in a workpiece being scanned by an ultrasonic sound beam, which formation reflects back to the probe from which the ultrasonic sound beam emanates a proportion of the sound energy high enough to mask echoes generated by anomalies within the workpiece.

The term "echo-masked zone" means a zone of a workpiece adjacent to one or more return-reflecting formations of the workpiece, which zone is rendered uninspectable by ultrasonic sound echography because echoes from the return-reflecting formations mask echoes from any anomalies in that zone.

BRIEF DESCRIPTION OF THE DRAWINGS

FIG. 2A is a partial view of a corner of the workpiece of FIG. 2;

FIG. 3A is a partial view of a corner of the workpiece of FIG. 3;

FIG. 4 is a perspective view of a disc-shaped workpiece illustrating conventional radial, axial and circumferential orientations of ultrasonic sound beams relative to the workpiece;

FIG. 4A is a perspective view of a wedge-shaped segment of a disc-shaped workpiece having a plurality of concentric circular grooves and lands;

FIG. 4B is a section view in elevation of the wedge-shaped section of FIG. 4A;

FIG. 5A is a partial schematic plan view of the turntable area of the device of FIG. 5;

FIG. 5B is a schematic elevation view, partly in section, of the area of FIG. 5A;

FIG. 5C is a view, on an enlarged scale relative to FIGS. 5A and 5B, of a portion of the turntable fixture and showing workpieces affixed thereto;

FIG. 6 is a front view in elevation showing a test workpiece comprising a blade component of a turbine engine having a series of test dimples formed therein;

FIGS. 6A, 6B and 6C are section views taken, respectively, along lines A—A, B—B and C—C of FIG. 6;

FIG. 7 is a side view in elevation of the test workpiece of FIG. 6;

FIG. 8 is a perspective view of the workpiece of FIG. 6 schematically showing an ultrasonic sound probe oriented relative to the test workpiece in accordance with an embodiment of the present invention;

FIG. 8A is a view corresponding to FIG. 8 except that the probe is schematically illustrated in a conventional axial orientation;

FIG. 8B is a view corresponding to FIG. 8 except that the probe is shown in a conventional circumferential orientation;

FIG. 9 is a top plan view of the test piece of FIG. 6 schematically showing the probe in two orientations relative to the workpiece;

FIG. 9A is a view corresponding to FIG. 9, but showing a different orientation of the probe relative to the workpiece;

FIG. 10 is a print-out showing the results of the test workpiece of FIG. 6 by ultrasonic sound applied with the probe in a circum-axial orientation relative to the workpiece in accordance with an embodiment of the present invention;

FIG. 10A is a view corresponding to FIG. 10 but showing the results attained by ultrasonic sound applied with the probe in conventional axial orientation relative to the workpiece; and FIG. 10B is a view corresponding to FIG. 10 but showing the results attained by ultrasonic sound applied with the probe in conventional circumferential orientation relative to the workpiece.

DETAILED DESCRIPTION OF THE INVENTION AND PREFERRED EMBODIMENTS THEREOF

Figure 1:
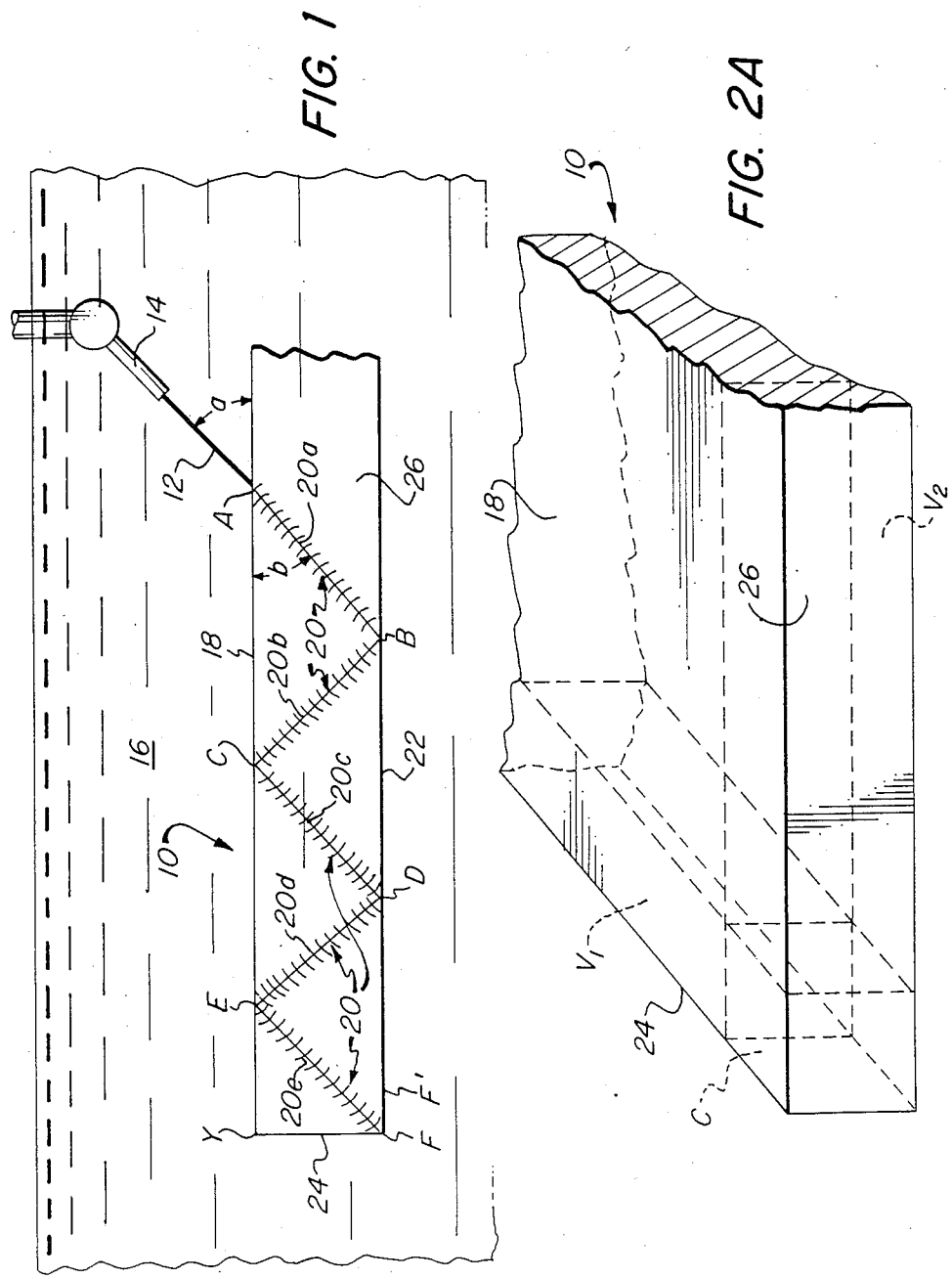
FIG. 1 is a schematic view in side elevation of a rectangular plate-shaped workpiece being scanned with an ultrasonic sound transducer.

Referring now to FIG. 1, a workpiece 10 comprising a flat, rectangular plate is shown in side elevation with a part of it broken away. Workpiece 10 will usually comprise steel or some other metal but, for clarity of illustration, is shown as being transparent to the sound waves directed into it from a beam 12 of ultrasonic sound pulses emitted from a conventional ultrasonic probe 14. Workpiece 10 has an inspection surface 18, an opposite lower surface 22, and an edge wall 24. Beam 12, which may be a focused beam, is directed through a transmission medium comprising a body of water 16 contained within a tank (not shown); workpiece 10 and probe 14 are immersed in the body of water. The focused beam 12 lies in a plane which is perpendicular to inspection surface 18. (The plane in which the focused ultrasonic beam lies is sometimes below referred to as the "scanning plane" of the beam or sound probe.) Beam 12 is directed onto inspection surface 18 of workpiece 10 at an angle of incidence a (relative to inspection surface 18) and generates a shear sound wave 20 which enters workpiece 10 at point A and is transmitted through workpiece 10 as a first leg 20a of sound wave 20. Leg 20a is at an angle of refraction b (relative to surface 18) which differs from the angle of incidence a, due to refraction of sound wave 20 by workpiece 10. While FIG. 1 is described with specific reference to a shear wave, the techniques of the present invention are utilizeable with any suitable type of ultrasonic sound wave including, in addition to shear waves, refracted longitudinal sound waves. At point B, the sound wave 20 is reflected from the lower surface 22 to inspection surface 18 as a second leg 20b, and so on, from points C, D and E as legs 20c, 20d and 20e of sound wave 20. Leg 20e is transmitted to point F, which is at the intersection of edge wall 24 with lower surface 22.

As will be appreciated by those skilled in the art, a large proportion of the sound energy directed at point A is reflected therefrom away from workpiece 1 and a much smaller proportion goes into generating the sound wave 20. Similarly, there is continued diminution of sound energy at each succeeding point B, C, D and E so that only a minor and diminishing (with each leg) proportion of the energy emitted from probe 14 is involved beyond the initial leg 20a. An oscilloscope screen display of the reflected sound wave 20 will therefore show the typical blip or echo peak at point A and a second, smaller peak at point B with the size of subsequent peaks (generated at points C, D, E, etc.) being greatly reduced because of the diminished sound energy beyond point B. This factor, and the time delay, substantially eliminate interference by echoes generated "downstream" of point B. Thus, when beam 12 impinges at point A any energy peaks or blips intermediate points A and B, which indicate the presence of an anomaly in that zone of workpiece 10, are clearly displayed, e.g., on an oscilloscope screen and/or on a graphic printout. Pinholes or cracks in the vicinity of leg 20a will reflect the sound wave at a characteristic angle and create a discernable echo intermediate those corresponding to points A and B.

Controlled relative movement is established between workpiece 10 and probe 14 so that the point of impingement of the focused beam 12 of ultrasonic energy upon inspection surface 18 moves in continuous, usually parallel scanning lines across the inspection surface 18. Typically, probe 14 would traverse workpiece 10 in a series of parallel, straight line paths extending from side wall 26 to a side wall (not shown in FIG. 1) opposite side wall 26, with each successive path advancing closer to edge wall 24 by an increment equal to the effective diameter of beam 12.

With the illustrated arrangement, successive zones of workpiece 10 may be inspected without difficulty until the point at which focused beam 12 impinges at point E, at which juncture the sound energy directed along the path of leg 20e, upon impinging at point F, is reflected back to point E and thence to the probe 14. This reflected sound energy is very large compared to the amount of sound energy which would be reflected back by a small anomaly in workpiece 10 along the path of leg 20e. The echo from point F to the probe 14 will mask the much smaller echo from any anomaly in the structure, resulting in effectively blocking inspection of a zone of workpiece 10 bounded by side wall 24, and by a plane through workpiece 10 in which the path of leg 20e lies. The cross section of this uninspectable zone is defined by the closed quadrilateral figure EF'FY in FIG. 1. The width of the sound wave comprising leg 20e and the geometry at the corner of workpiece 10 effectively blind probe 14 from about the point where a leg of sound wave 20 hits point F' on lower surface 22.

Figure 2:
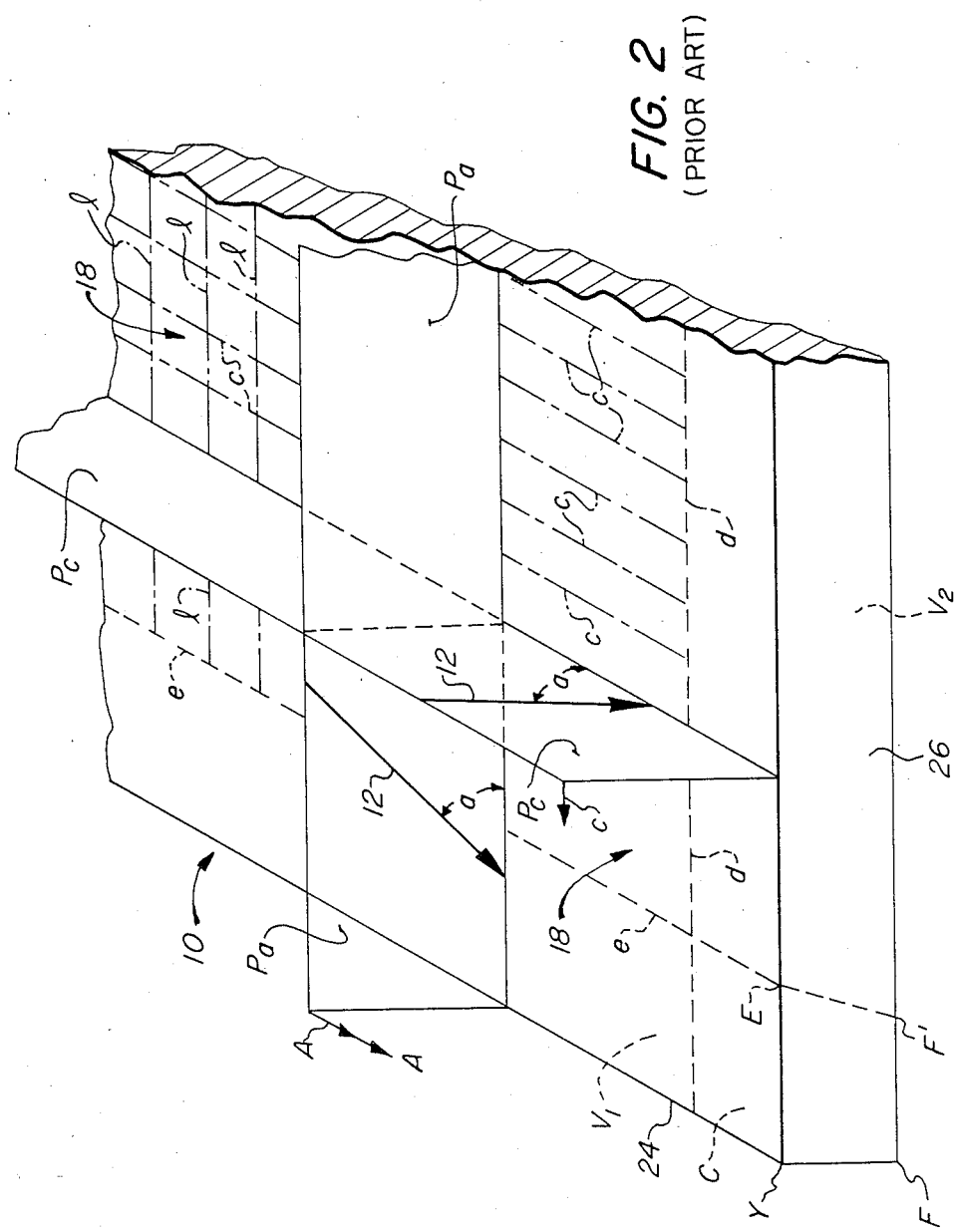
FIG. 2 is a schematic perspective view of the workpiece of FIG. 1 illustrating conventional mutually perpendicular orientation of the probe during two successive series of passes.

This inspection difficulty is well illustrated in FIG. 2, which shows two typical scanning planes oriented relative to workpiece 10 in accordance with prior art practices. Thus, probe 14 (FIG. 1) will, in accordance with the prior art practice, make a first series of inspection passes with beam 12 inclined at an impingement angle a to inspection surface 18 and successively positioned in a series of axial scanning planes, a typical one of which is shown as Pa. The arrow A associated with plane Pa indicates the direction of subsequent deployment of axial planes. The path of beam 12 along inspection surface 18 on preceeding axial passes is indicated by dot-dash lines 1 and it is seen that the axial scanning planes lie parallel to side wall 26 and perpendicular to edge wall 24, which comprises a back-reflecting formation and creates the quadrilaterally-shaped echo-masked zone $V_1$ (the cross section of which is shown at EF'FY in FIG. 1) lying adjacent to edge wall 24. A boundary of this echo-masked zone is indicated in FIG. 2 by dash line e. Lines 1 stop at the boundary e to indicate the extent of useful inspection; however, in practice, the beam 12 is usually continued to the edge wall 24, even though the last part of its traversal prior to encountering edge wall 24 will not provide useful inspection. It is usually simpler to traverse the entire workpiece, especially as the shape of the echo-masked zone changes in more complexly-shaped workpieces. Inspection passes will normally be continued until an inspection pass is completed in an axial scanning plane which lies immediately adjacent to side wall 26.

Still in accordance with prior art practices, a second series of inspection passes is carried out with beam 12 impinging on inspection surface 18 at an impingement angle a but lying in respective, so-called circumferential scanning planes, a typical one of which is shown as Pc in FIG. 2, with arrow C indieating the direction of deployment of subsequent circumferential scanning planes. The path of impingement of beam 12 during inspection passes in preceeding circumferential scanning planes is indicated by dot-dash lines c. These passes will be continued until an inspection pass is completed in a circumferential scanning plane which lies immediately adjacent and parallel to edge wall 24. With respect to the circumferential scanning passes, side wall 26 acts as a return-reflecting structure, which results in a quadrilaterally-shaped echo-masked zone $V_2$, a border of which is shown as dash line d in FIG. 2.

The result of the two series of mutually perpendicular passes of inspection is shown in FIG. 2A, in which a substantially cubic corner zone C, defined by the overlapped of zones $V_1$ and $V_2$ is entirely uninspected and in which the remainder of the echo-masked zones $V_1$ and $V_2$ have been inspected only in a single, (axial or circumferential) direction. Assuming that workpiece 10 is of rectangular plate configuration, there will be a total of four uninspected corner zones, of which C is typical, and four zones (of which the zones $V_1$ and $V_2$ less the overlapped corner portions corresponding to C are typical) which have been inspected by only a single direction of passes. It is clear that a significant volume of the workpiece 10 is left uninspected, or under-inspected. As is well known in the art, a small imperfection or anomaly in the formation of a workpiece may make it transparent, or nearly so, to an ultrasonic sound wave which impinges upon it axially, but may provide a pronounced echo when a sound wave of the same intensity strikes it transversely to its longitudinal axis. For this reason, two inspection passes at mutually perpendicular orientation are usually needed in each region for adequate inspection. Because of the relatively large uninspectable volume remaining after such inspection, parts are sometimes made oversize, inspected and then machined to their final dimension, which removes most or all of the uninspectable area. However, this is obviously an uneconomical procedure as it wastes the material which must be machined away and requires a post-inspection manufacturing step. The economic penalty is particularly severe with parts made from expensive materials such as titanium blades in jet engines.

Figure 3:
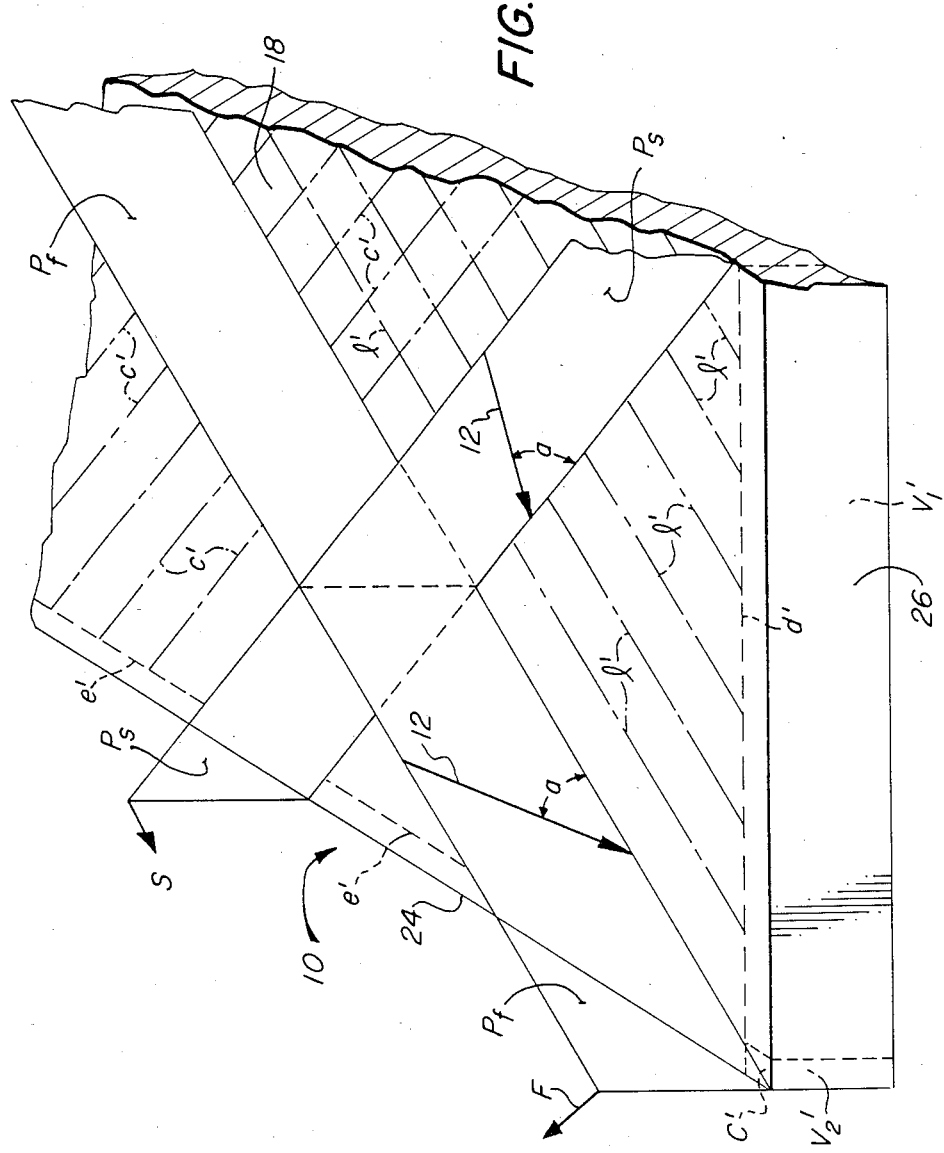
FIG. 3 is a schematic, perspective view corresponding to FIG. 2 but showing the orientation of the probe relative to the workpiece during two successive series of passes in accordance with an embodiment of the present invention.

Referring now to FIG. 3, there is shown the same workpiece 10 as illustrated in FIG. 2, in the same orientation as illustrated in FIG. 2, i.e., showing inspection surface 18 at the top, edge wall 24 at the left and side wall 26 at the foreground as viewed in FIG. 3. However, in FIG. 3 the scanning planes are shown positioned in accordance with an embodiment of the present invention to provide dual direction inspection over a much larger volume of the workpiece 10. This is attained by setting up the work to position the probe 14 (FIG. 1) relative to workpiece 10 so that the focused sound beam 12 is directed at an impingement angle a relative to inspection surface 18 in a first series of scanning planes, a typical one of which is indicated at Pf in FIG. 3 and a second series of planes, a typical one of which is indicated as Ps. The arrows F and S respectively indicate the direction of subsequent deployment of planes Pf and Ps. These planes may be referred to as circum-axial planes, because they have an orientation to the workpiece which is intermediate the conventional axial and circumferential orientation. The path of beam 12 along inspection surface 18 and preceeding ones of the first series of circum-axial passes is indicated by dot-dash lines 1' and the corresponding paths of beam 12 during preceeding ones of the second series of passes is indicated by dot-dash lines c'. Plane Pf is perpendicular to plane Ps and both are non-perpendicular to edge wall 24 and to side wall 26 of workpiece 10. Planes Pf and Ps therefore respectively define non-perpendicular angles of incidence at the points at which edge wall 24 and side wall 26 are intersected by planes. This non-perpendicular orientation of the scanning planes relative to the return-reflecting formations will, if edge-wall 24 and side wall 26 have a sufficiently smooth finish, provide two passes of inspection extending all the way to the walls 24 and 26. In this case, the only uninspected zone will be corner zone C' (FIG. 3A) at the intersection of edge wall 24 and side wall 26. For the same workpiece, uninspectable corner zone C' resulting from the techniques of the invention will be significantly smaller than the uninspectable corner zone C of FIG. 2A resulting from conventional inspection techniques with the scanning planes perpendicular to walls 24 and 26.

In the case where edge wall 24 and side wall 26 are sufficiently rough, a peripheral echo-masked zone bounded by walls 24 and 26 will result even when using the techniques of the present invention. However, this peripheral echo-masked zone will be smaller than that resulting from the prior art techniques so that even with rough, sound-scattering edge and side walls, the technique of the present invention reduces the total volume of the echo-masked zones as compared to the prior art techniques (illustrated in FIG. 3) of orienting the scanning planes perpendicularly relative to the return-reflecting structures or formations. A worst-case situation using the technique of the present invention occurs when edge wall 24 and side wall 26 are rough enough to provide a pronounced sound-scattering effect. The resultant uninspectable zones are illustrated in FIG. 3 by showing a peripheral echo-masked zone in workpiece 10, a border of which is indicated in FIG. 3 by dash lines d' and e' in inspection surface 18. Only the thin peripheral zones between planes perpendicular to inspection surface 18 and passing through dash lines d' and e' and walls 24 and 26, is left uninspected. Thus, in this worst-case scenario, dual direction inspection is attainable throughout the workpiece 10 except for the rather thin peripheral border segment, indicated as zones $V_1'$ and $V_2'$. As noted above, zones $V_1'$ and $V_2'$ are dual-pass inspectable if walls 24 and 26 are reasonably smooth.

The enhanced volume of inspection attainable using the non-perpendicular arrangement illustrated in FIG. 3 may be understood by analogy to shining a focused beam of light upon the surface of a mirror. If the axis of the beam is directed perpendicularly to the mirror, the light will be reflected from the mirror directly back to the flashlight lens. A corresponding arrangement with an ultrasonic sound wave will provide a high amplitude echo comprising the energy reflected from the surface of the workpiece, which will be orders of magnitude greater than the amplitude of an echo which would be attained by reflection from a crack, pinhole or other miniscule anomaly in the workpiece. On the other hand, if the flashlight is shined upon the mirror at a non-perpendicular angle to the mirror surface, the light from the focused beam of the flashlight will be reflected at an angle and the reflected beam will not impinge upon the flashlight lens, thus permitting the flashlight to approach much closer to the surface of the mirror before it is "blinded" by its own reflection.

In setting up the inspection procedure, the orientation of the probe relative not only to edges, but to corners, lands and other return-reflecting formations provided by the workpiece to be inspected are taken into consideration As illustrated below, this usually makes for more complicated set-up calculations than does the straight-forward axial and/or circumferential and/or radial orientation employed by the prior art, but the enhanced quality and extent of inspection will justify the extra effort required.

FIG. 4 shows a disc-shaped workpiece 10' having a circular-shaped, flat inspection surface 18' and a peripheral, cylindrical-shaped inspection surface 18''. Inspection surface 18" is the side wall or edge of the disc and provides a return-reflecting formation relative to flat inspection surface 18' (and relative to the unnumbered surface opposite to surface 18'). Correspondingly, the peripheral portion of inspection surface 18' (and of the unnumbered surface opposite it) provide return-reflecting formations relative to cylindrical-shaped inspection surface 18".

The center of the disc-shaped workpiece 10' is indicated at CR, the center of rotation of the workpiece 10' about its own longitudinal axis. The plane Pr is a radial scanning plane in which lies a beam 12r of ultrasonic sound for impingement upon surface 18'. Plane Pc, a circumferential scanning plane, intersects surface 18' along a chord of the circle defined by surface 18' and a beam 12c of ultrasonic sound is shown lying within plane Pc. Plane Pa is an axial scanning plane and oppositely directed beams 12a-1 and 12a-2 of ultrasonic sound are depicted as lying therein and impinging upon surface 18".

Surface 18' may be inspected by rotating workpiece 12' about its longitudinal axis (extending vertically to surface 18' through center of rotation CR), i.e., as if workpiece 10' were a phonograph record. Simultaneously, beam 12r would be advanced in the manner of a phonograph needle along a radius line between the periphery and point CR of surface 18' of the workpiece. This would orient beam 12r in an infinite series of scanning planes Pr intersecting inspection surface 18' like the spokes of a wheel whose rim is surface 18". A similar approach could be employed circumferentially oriented with sound beam 12c. Sound beam 12a-1 could be traversed vertically within axial plane Pa between inspection surface 18' and its opposite, unnumbered surface while workpiece 10' is rotated about its longitudinal axis. A second series of passes could similarly be made with the ultrasonic sound beam 12a-2 positioned within plane Pa but at an azimuth angle relative to surface 18" opposite that of beam 12a-1. Of course, workpiece 10' could remain stationary while the probe or probes (not shown in FIG. 4) from which beams 12r, 12c, 12a-1 and 12a-2 emanate are moved relative to workpiece 10'.

Workpieces of complex configuration, which present many more return-reflecting formations and corresponding echo-masked zones than the simple plate of workpiece 10 or the simple disc of workpiece 10' must often be inspected. For example, FIG. 4A shows a wedge or pie slice-shaped segment of a circular disc workpiece 72 having a central aperture 73, and plurality of stepped, concentric grooves 74 and lands 76 formed therein. The peripheral edge of workpiece 72 is defined by a cylindrical shaped wall 78. The grooves 74 and lands 76 are defined by numerous side walls (unnumbered) which, together with peripheral wall 78, provide a plurality of return-reflecting formations and consequent echo-masked zones. With the numerous sidewalls, some of which are vertical relative to the plane of disc 72, and others of which are sloped at an angle, the practitioner skilled in the art would tend to orient the focused beam of ultrasonic sound along the diameter of disc 72 for a first series of radial passes, because the set-up for such a radial orientation is relatively simple.

It will be appreciated that conventional axial, radial and/or circumferential inspection of a workpiece such as that of FIG. 4, although relatively simple to set up, would result in a large volume of echo-masked zones. The ability of the present invention to substantially reduce the volume of the echo-masked zones by the non-perpendicular orientation of the sound beams relative to the numerous return-reflecting formations provides very significant practical advantages in inspecting articles such as disc 72.

FIG. 4B shows a cross section of a radial half of the workpiece 72, indicating at dot-dash line CR its longitudinal axis, passing through the center of central aperture 73 of the workpiece 72. The orientation of axially oriented ultrasonic sound beams 12a-3 and 12a-4, and radially oriented beams 12r-1 and 12r-2 are shown. Conventionally, beams 12a-3, 12a-4, 12r-1 and 12r-2 would lie in planes passing through axis CR, i.e., in the plane of the drawing of FIG. 4B. As shown in FIG. 4A, the ultrasonic sound beams 12ca-1 and 12ca-2 oriented relative to workpiece 72 in accordance with an embodiment of the present invention lie in planes intermediate radial and circumferential planes like planes Pr and Pc of FIG. 4. Similarly, beams 12ca-3 and 12ca-4, also oriented in accordance with the teachings of the present invention, impinge on the cylindrical shaped wall 78 of workpiece 72 and lie in planes transverse to axial planes such as plane Pa of FIG. 4. That is, beams 12ca-3 lie in planes which do not pass through the longitudinal axis CR of workpiece 72.

Figure 5:
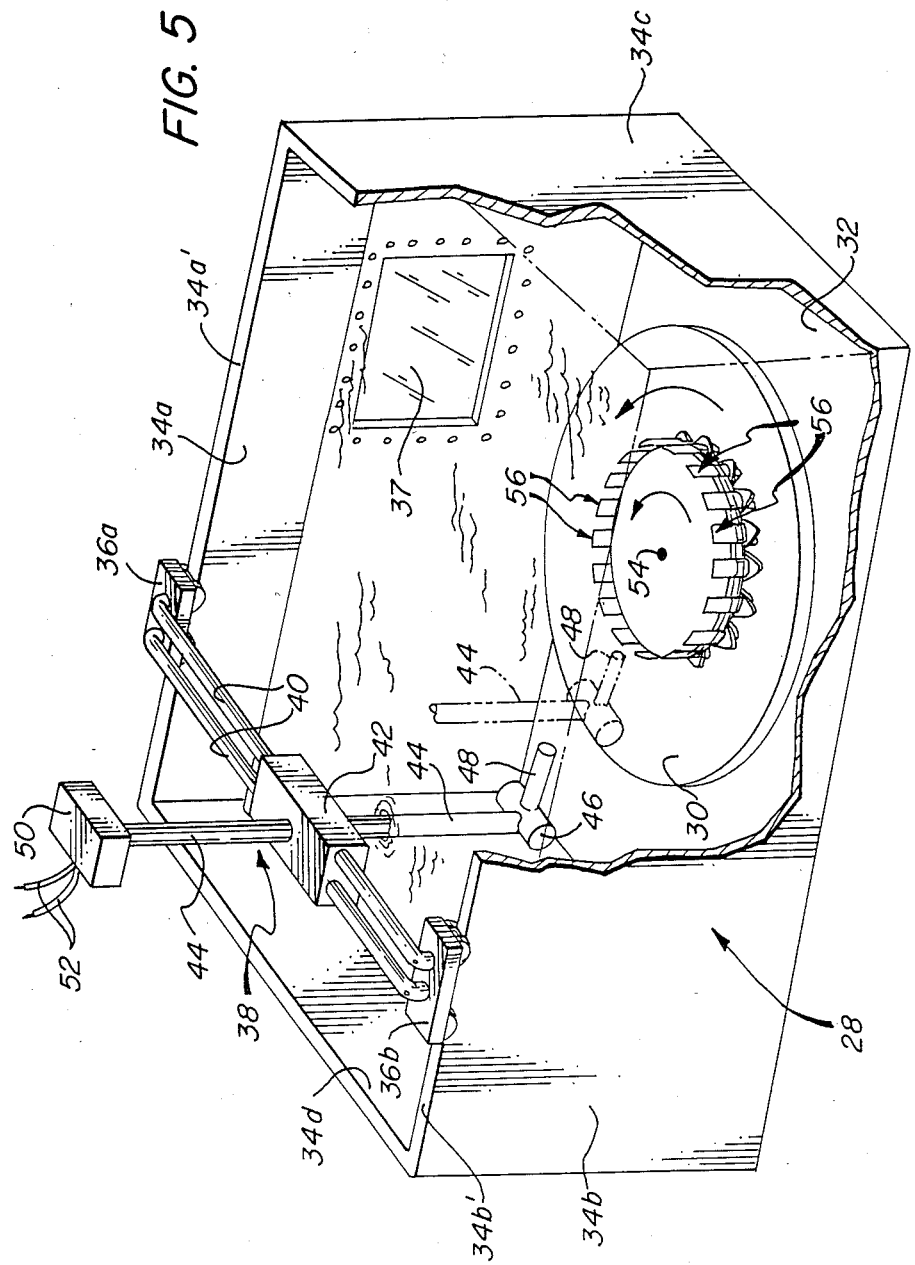
FIG. 5 is a perspective view, with parts broken away and other parts omitted for ease of illustration, of an ultrasonic testing immersion tank equipped with a turntable on which a mounting jig or fixture is carried.

For testing purposes, ultrasonic sound waves require a transmission medium denser than air between the transducer and the workpiece, and so a liquid medium, usually water, is employed. In immersion test techniques, both the probe containing the ultrasonic transducer and the workpiece are immersed in water. A typical immersion test tank is shown in FIG. 5 and comprises a water-tight tank 28, which is of generally rectangular configuration, having a floor 32 and vertical sides 34a, 34b, 34c and 34d; tank 28 contains a body of water therein. An observation window 37 is provided in wall 34a to permit convenient visual observation into the tank. Walls 34b and 34c are partly broken away for purpose of illustration to reveal a turntable 30 mounted on the floor 32 of the tank for rotation about its center of rotation CR (FIG. 5A) on a central post 64 (FIG. 5B) carried in a water-tight packing bearing 66 and having thereon a pulley (unnumbered) on which is carried a drive belt 68, partially broken away in FIG. 5B. Drive belt 68 is driven by an electric motor, not shown, at a selected speed to rotate turntable 30 at a desired rate of revolutions per minute. As is conventional, the drive belt is located outside of tank 28, beneath the floor 32 thereof.

The top edges 34a' and 34b' of walls 34a and 34b form tracks on which are respectively received trolleys 36a and 36b of an adjustable ultrasonic search unit 38. A pair of spaced-apart bridge members 40 connect trolley 36a to trolley 36b and support at their midpoint a drive box 42 within which is mounted a probe support rod 44. Drive box 42 is movable along member 40, between trolleys 36a and 36b. A probe 48 is carried at the lower end of support rod 44 by means of a universal joint connector 46 which permits both vertical and horizontal swiveling of probe 48. The connector 46 is constructed in a manner well known in the art so as to permit probe 48 to be placed into a given skewed position displaced both horizontally and vertically from its normal position in which the longitudinal axis of probe 48 is at a right angle to the longitudinal axis of rod 44 and aligned in a vertical plane passing through the center of turntable 30. A control box 50 surmounts support rod 44 and has connected to it cables 52 which contains suitable electrical leads to control the positioning of adjustable search unit 38 and swiveling movement of probe 48, and to transmit and receive ultrasonic signals through the transducer contained within probe 48. Since adjustable search unit 38 is movable along the tracks provided by top edges 34a' and 34b', probe 48 may be positioned at a selected distance relative to turntable 30. Drive box 42 is moveable along bridge members 40 and so enables probe 48 to be laterally positioned as desired, either aligned with the center of rotation of turntable 30 (as shown in FIG. 5A) or laterally off-set to either side thereof (as shown in phantom outline in FIG. 5A). Support rod 44 is postionable vertically in drive box 42, to position probe 48 at a selected elevation within tank 28. The construction and capabilities of adjustable search unit 38 are conventional in the art as is the entire apparatus illustrated in FIG. 5.

In the particular test set-up illustrated in FIG. 5, a jig or fixture 54 is mounted at the center of turntable 30 by any suitable means for rotation of fixture 54 with turntable 30 about a common center of rotation CR. Fixture 54 is itself disc-shaped and of a smaller diameter than turntable 30 and has fixed about the peripheral wall 54a thereof a plurality of workpieces comprising, in the illustrated instance, a plurality of turbine engine blades 56 of the type illustrated in FIGS. 6 and 7. As shown in FIG. 6, turbine blades 56 comprise a root 58, a flange 60 and a curved vane 62 having a top edge 62a, a leading edge 62b and a feathered, trailing edge 62c. Vane 62 has a concave surface 62v and a convex surface 62x. A typical inspection requirement for blades 56 calls for inspecting the portion of vane 62 adjacent to top edge 62a, for example, inspecting a zone of the vane 62 which is bounded by top edge 62a and extends for a short distance, such as 0.080 inches (0.203 cm), from top edge 62a toward root 58. Blades such as blades 56 may be made of a titanium alloy and after use are re-built by welding to re-build top edge 62a. Ultrasonic sound inspection in accordance with the present invention is advantageously employed to examine the weld re-built area for flaws or discontinuities.

For test purposes, a plurality of the blades 56 may be mounted about the periphery of fixture 54, as illustrated in FIG. 5C, by taping or otherwise affixing the vanes 62 to the peripheral edge of fixture 54 with each of the blades positioned at the same vertical elevation within tank 28. A tape 70 is shown in FIG. 5C as wrapped about the vanes 62 to hold blades 56 in place against vertical peripheral wall 54a. The blades are equally spaced about the periphery of fixture 54 with vanes 62 positioned in an upright or vertical position with their convex surface providing the inspection surface onto which the ultrasonic sound pulses are impinged. Only two of the blades 56 are illustrated in FIG. 5C, but it will be appreciated that a plurality of such blades may be mounted in non-overlapping or slightly spaced-apart relationship about the entire peripheral wall 54a. With this set-up, rotation of the turntable 30 will repeatedly traverse each of the blades 56 across the emitting end of probe 48 for traversal of the ultrasonic focused sound beam 12 across the vane portion 62 of each of blades 56. The adjustable ultrasonic search unit 38 will be positioned to place its probe 48, suitably oriented, in a position, indicated in dash outline in FIG. 5, to scan each of the mounted blades 56 as it passes before probe 48. After fixture 54 completes one revolution, each blade will have been scanned in one pass by probe 48. Probe 48 is then raised by support rod 44 a small, incremental amount and a second inspection pass is made at an elevation slightly above the first pass as turntable 30 (and therefore fixture 54) continues to rotate. Probe 48 is gradually raised in incremental amounts upon the completion of each revolution of fixture 54 to provide a series of inspection passes along substantially parallel first planes. In accordance with the present invention, the set-up will be arranged so that probe 48 is positioned in a skewed, circum-axial attitude intermediate the conventional axial and circumferential orientations. After the first series of passes is completed, the probe 48 is reoriented to an oppositely skewed position, and the second series of passes may be made with the focused beam 12 lying in scanning planes which are substantially perpendicular to those of the first series of planes.

Tests utilizing the circum-axial orientation techniques of the present invention and, for comparison purposes, conventional axial and circumferential orientation techniques of the prior art were carried out. All tests were carried out using the same equipment and the same test pieces, with the only variation being the type of orientation employed for the ultrasonic probe. The equipment employed for the tests was a Krautkramer-Branson, Inc. KB 6000 device equipped with a ¼ inch (0.635 cm) diameter, 15 megaherz Harrisonic immersion transducer providing a focused beam with a one-inch (2.54 cm) focal length.

A single test piece as illustrated in FIG. 6 was employed, having three test dimples 61a, 61b and 61c formed therein. The depth and diameter dimensions of the test dimples are set forth below, d1, d2 and d3 representing the respective diameters of the test dimples and $h_1$, $h_2$ and $h_3$ representing their corresponding depths, as shown in FIGS. 6A, 6B and 6C. Each of the test dimples is circular in plan view and is centered 0.040 inches (0.102 cm), indicated by the distance R in FIG. 6, below the top edge 62a of blade 56. At top edge 62a, vane 62 is 0.040 inches (0.102 cm) thick and the shape of its convex surface 62x approximates a section of a circular cylinder well.

TABLE

| Dimple | Diameter (inches) | Depth (inches) |
| --- | --- | --- |
| 61a | d1 = 0.0057 | $h_1$ = 0.0026 |
| 61b | d2 = 0.0055 | $h_2$ = 0.0056 |
| 61c | d3 = 0.0055 | $h_3$ = 0.0018 |

In each of FIGS. 8, 8A and 8B, probe 48 is shown schematically, the focused sound beam 12' impinges upon the inspection surface (convex surface 62x) and penetrates vane 62 as sound wave 20', and a cross-sectional shape outline of vane 62 is indicated at S.

COMPARATIVE EXAMPLE 1

Scanning of the test piece, a titanium turbine blade as illustrated in FIGS. 6 and 7, was carried out in the conventional manner, employing axial and circumferential orientation of the probe in two series of inspection passes. The set-up was calculated as follows.

A refraction angle of the shear sound wave in the workpiece (corresponding to angle b in FIG. 1) of 45° is desired and the impingement angle (corresponding to angle a in FIG. 1) required to attain the 45° refraction angle in the titanium is calculated according to Snell's Law which holds that $$\frac{\sin a}{\sin b} = \frac{V_w}{V_m} \quad (1)$$

wherein a is the angle of incidence, b is the angle of refraction, $V_w$ is the velocity of sound in water and $V_m$ is the shear wave velocity of sound in the metal of the workpiece. Substituting $V_w = 1.48 \times 10^5$ cm/sec, $V_m = 3.11 \times 10^5$ cm/sec and b=45° in equation (1) and solving for a, shows that a=19.6638°. Therefore, the beam of sound should impinge upon the workpiece surface at an angle of 19.66° to give a 45° refracted shear wave in the workpiece.

In order to position the probe properly relative to a convex surface such as inspection surface 62x of vane 62 for circumferential shear inspection, an offset x (FIG. 9) from the axial centerline $D_t$ must be calculated. If the radius of curvature of convex surface 62x is taken as R, then the offset x is calculated as $$x = R(\sin a) \quad (2)$$

Offset x is shown in FIGS. 7 and 9. For vane 62, suface 62x is substantially a section of a cylinder having an outside diameter of 6.9 inches (17.53 cm) and substituting R=3.45 inches and a=19.66° in equation (2), the offset x is calculated as 1.1609 inches (2.949 cm). Therefore, in order to achieve a circumferential shear scanning plane relative to inspection surface 62x, the probe is positioned on center line $D_t$ pointing perpendicularly at surface 62x, moved in a horizontal (circumferential) plane 1.1609 inches off the axial centerline $D_t$. Because of the curvature of inspection surface 62x, the resultant impingement angle will have the calculated value of 19.66°.

As an alternate technique, the probe 48 may be turned 19.66° in the circumferential plane and then shifted relative to centerline $D_t$ to return the point of impingement of the beam to the centerline $D_t$.

Whichever of the two techniques is utilized, the probe is now positioned to conduct a series of inspections by rotating the workpiece past the probe. With reference to FIG. 5, this is carried out by mounting the workpiece on the fixture 54 and rotating the turntable 30 at a selected speed. After the workpiece makes a pass past the probe, the probe is lowered 0.001 inches (0.00254 cm) for a second scanning pass adjacent to and immediately below the first. This is repeated as necessary to cover the test distance from the top edge of the blade to a selected stopping point.

The probe is then returned to the centerline and displaced by the calculated offset of 1.1609 inches in a direction opposite the first offset and the probe is rotated in the circumferential plane the calculated angle of 19.66° in a direction opposite to the angulation for the first series of circumferential passes. The test passes are then repeated to provide a second series of circumferential passes at an azimuth angle relative to inspection surface 62x opposite that used in the first series of passes.

In order to calculate the correct setting for axial shear inspection, the probe is positioned on the axial centerline $D_t$ and pointed perpendicularly at the surface 62x. The probe is then rotated upwardly in a vertical plane to the calculated incidence angle of 19.66° so that the beam impinges on surface 62x a vertical distance y (FIG. 7) above the horizontal plane in which the probe lies when it is oriented perpendicularly to surface 62x.

A first series of passes is then made to provide an axial inspection. Because in this particular inspection only a distance of 0.080 inches (0.203 cm) from top edge 62a is being inspected, only one series of axial inspections is made.

FIG. 8A is a schematic representation in which the probe 48 is positioned for the first series of passes in the axial orientation illustrated in FIG. 8A and, for the second series of passes, in the circumferential orientation illustrated in FIG. 8B. FIG. 9 shows probe 48 in two positions near opposite ends of a traverse of the workpiece (blade 56) and with probe 48 (and, therefore, beam 12') aligned parallel to diameter Dt (FIG. 4A) of turntable 30 and fixture 54. FIG. 9A shows probe 48 (and, therefore, beam 12') aligned at an angle to diameter Dt. In both FIG. 9 and FIG. 9A, the beam 12' is circum-axially oriented relative to blade 56, in accordance with the present invention. The scanning results obtained are illustrated in FIGS. 10A and 10B in which it is seen that reflections from top edge 62a during the axial orientation of the probe have substantially entirely masked the echoes produced by the test dimples. In FIG. 10B, during the circumferential orientation of the probe, the test dimples are clearly shown but large segments of the volume are masked as indicated by the areas M1, M2 on the printout of FIG. 10B.

EXAMPLE 2

The same equipment was used to scan the same test piece as in Example 1, except that the test probe was oriented in two series of passes in the circum-axial configuration in accordance with an embodiment of the invention, as follows.

The required angle of incidence to attain a desired shear angle is calculated in the conventional manner using Snell's Law. Since the same blade as tested in Example 1 is to be tested, and a refraction angle within the blade of 45° is desired, the same angulation of 19.66° is utilized.

In order to calculate the proper angulation for the probe, a vector of probe pivoting movement in a vertical (axial) plane must be calculated and a corresponding calculation must be made for a corresponding vector of probe pivoting movement in a horizontal (circumferential) plane. The resultant of these two vectors will give the required angulation of the probe to conduct an inspection of surface 62x with the probe oriented circum-axially, in accordance with an aspect of the present invention.

The distance y (FIG. 7) may be calculated as follows:

$$y = \tan a' \quad (2)$$

The angle a (FIG. 9) is a function of the offset distance x because of the curvature of surface 62x. The distance from the probe pivot point (P in FIGS. 7, 9 and 9A) to the curved surface 62x for the circum-axial scan must be calculated.

If surface 62x were flat, then the Pythagorean theorem could be utilized to derive the distance from the probe pivot point P to the inspection surface 62x; for a slightly curved surface, it gives an approximation of the required distance. The calculations show that a 14.2° axial movement of the probe and a 14.2° circumferential movement of the probe positions the probe in the desired circum-axial orientation to give the desired 19.66° impingement angle.

The results obtained in two mutually perpendicular circum-axially oriented passes are shown in FIG. 10, from which it is seen that the presence of the test dimples is clearly delineated and the edge masking effect, indicated by the dark areas M1' and M2', is practically negligible.

Although specific embodiments of the invention are described in detail using a single probe to generate the ultrasonic sound beam, it will be appreciated that, as known in the art, multiple probes may be employed to emit a plurality of beams onto the workpiece. In such case, a single pass of the workpiece past the multiple probes will provide a series of individual scanning passes.

What is claimed is:

1. In an ultrasonic sound scanning method for detection of ultrasonic anomalies in a workpiece having an inspection surface and at least one formation which results in an echo-masked zone in the workpiece, the method including carrying out an inspection pass by (a) directing a beam of ultrasonic sound pulses from a probe along a beam axis through a transmission medium and impinging the beam upon the inspection surface at a selected impingement angle and thence into the workpiece, (b) receiving echo pulses thereby reflected from the workpiece, (c) displaying the echo pulses to reveal those, if any, which indicate the existence of anomalies within the workpiece, and (d) traversing the beam in a pre-selected path along the inspection surface, the improvement comprising: making one or more first inspection passes with the probe oriented so that, relative to the workpiece, the beam lies within one or more first scanning planes which are non-perpendicular to at least one said return-reflecting formation at its point or respective points of intersection with the first plane or planes, whereby to reduce the volume of the echo-masked zone relative to that which would be generated with the probe oriented in a corresponding number or one or more scanning planes which are perpendicular to said at least one return-reflecting formation.

2. The method of claim 1 including making a first series of said first inspection passes so that the beam successively lies within a series of said first scanning planes.

3. The method of claim 2 including making a second series of inspection passes with the probe oriented so that the beam lies in a series of second scanning planes which intersect said first scanning planes.

4. The method of claim 3 wherein said series of second scanning planes are perpendicular to said first scanning planes.

5. The method of claim 1 or claim 2 wherein the beam of ultrasonic sound pulses is a focused beam.

6. The method of claim 1 or claim 2 wherein the inspection surface is a curved surface.

7. The method of claim 6 wherein the inspection surface is a convex surface.

8. The method of claim 1 or claim 2 wherein the inspection surface is intersected by a plurality of return-reflecting formations.

9. The method of claim 1 or claim 2 wherein the transmission medium is water.

10. A method of ultrasonic sound scanning for detection of ultrasonic return-reflecting anomalies in one or more workpieces having inspection surfaces and one or more return-reflecting formations which result in one or more echo-masked zones in the workpiece, the method comprising:
    establishing relative movement within a transmission medium between the one or more workpieces and a probe from which a beam of ultrasonic sound pulses emanates, and directing the beam along a beam axis through the transmission medium, and impinging the beam upon the inspection surface at a selected impingement angle and thence into the workpiece;
    maintaining the relative movement to traverse the beam in a pre-selected path along the inspection surface with the probe oriented so that, at least when the beam impinges the workpiece in the vicinity of said return-reflecting formations, the beam successively lies within a series of first scanning planes which are non-perpendicular to at least one of said return-reflecting formations at its respective points of intersection with the first scanning planes, whereby to reduce the volume of the echo-masked zone relative to that which would be generated with the probe oriented in a series of scanning planes which are perpendicular to said return-reflecting formation;
    receiving echo pulses reflected from the workpiece;
    displaying the echo pulses to reveal those, if any, which indicate the existence of anomalies within the workpiece.

11. The method of claim 10 including carrying out the establishing and maintaining of the relative movement between the one or more workpieces and the probe by maintaining the probe in a series of fixed positions and transporting the one or more workpieces past the probe while the probe is held in respective fixed positions in order to traverse the beam in the pre-selected path along the inspection surfaces.

12. The method of claim 11 including mounting a plurality number of workpieces on a turntable for rotation of each of the workpieces past the probe while the probe is in a given fixed position and, after each of the plurality of workpieces has been rotated past the probe, moving the probe to another of its fixed positions for rotation of each of the workpiece past it, and repeating the process for successive fixed positions of the probe.

13. The method of claim 12 wherein the workpieces have convex inspection surfaces and the return-reflecting structures comprise respective edges of the workpiece.

14. The method of claim 10 wherein the transmission medium is water.

15. The method of claim 10 wherein the beam of ultrasonic sound pulses is a focused beam.

* * * * *

UNITED STATES PATENT AND TRADEMARK OFFICE
CERTIFICATE OF CORRECTION

PATENT NO. : 4,805,459

DATED : February 21, 1989

INVENTOR(S) : Nicholas C. Ferreira

Page 1 of 3

It is certified that error appears in the above—identified patent and that said Letters Patent is hereby corrected as shown below:

Column 1, line 17, replace "characterisic" with --characteristic--

Column 2, line 20, replace "ininspectable" with --uninspectable--

Column 2, line 58, replace "some" with --zone--

Column 5, line 34, replace "1" with --10--

Column 6, line 13, replace "side wall 24" with --edge wall 26--

Column 6, line 57, replace "C" with --c--

Column 8, line 60, between "eration" and "As", add --.--

Column 9, line 22, replace "12'" with --10'--

Column 9, line 31, between "employed" and "circumferentially", insert --with--

Column 9, line 32, delete "with"

Column 9, line 66, replace "FIG. 4" with --FIG. 4A--

Column 10, line 15, between "12ca-2" and "oriented", insert --emanating from probes 14' and producing respective sound waves 20', are--

Column 10, line 17, between "invention" and "lie", insert --and--

Column 10, line 19, between "12ca-4," and "also", insert --(FIG. 4B)--

Column 10, line 23, between "12ca-3" and "lie", insert --and 12ca-4--

Column 10, line 68, replace "contains" with --contain--

Column 11, line 23, after "wall 54a", add --(FIGS. 5B and 5C)--

Column 11, line 30, after "surface 62x", add --(FIG. 7)--

UNITED STATES PATENT AND TRADEMARK OFFICE
CERTIFICATE OF CORRECTION

PATENT NO. : 4,805,459

DATED : February 21, 1989

INVENTOR(S) : Nicholas C. Ferreira

It is certified that error appears in the above—identified patent and that said Letters Patent is hereby corrected as shown below:

Column 12, line 53, between "62" and "as", insert --of blade 56--

Column 13, line 23, replace "FIGS. 7 and 9" with --FIG. 9--, replace "suface" with --surface--

Column 14, line 26, replace "M1, M2" with --$M_1$, $M_2$--

Column 14, line 53, replace "(2)" with --(z)-- in the mathematical equation

Column 15, line 5, replace "M1' and M2'" with --$M_1$' and $M_2$'--

Column 15, line 19, between "one" and "formation", insert

--return-reflecting--

Column 15, line 41, in the twenty-third line of claim 1, replace

"or" with --of--

Column 16, line 34, in the twenty-ninth line of claim 10, add the word --and-- immediately after "workpiece;"

Column 16, line 47, in the second line of claim 12, delete the word "number"

UNITED STATES PATENT AND TRADEMARK OFFICE
CERTIFICATE OF CORRECTION

PATENT NO. : 4,805,459

DATED : February 21, 1989

INVENTOR(S) : Nicholas C. Ferreira

It is certified that error appears in the above-identified patent and that said Letters Patent is hereby corrected as shown below:

Column 16, line 52, replace "workpiece" with --workpieces--

Signed and Sealed this

Twenty-ninth Day of May, 1990

Attest:

HARRY F. MANBECK, JR.

*Attesting Officer*  *Commissioner of Patents and Trademarks*